United States Patent

[19]

Martin et al.

[11] Patent Number: 5,845,847
[45] Date of Patent: Dec. 8, 1998

[54] AIR FRESHENER DISPENSER DEVICE

[75] Inventors: John Martin, Caledonia; Joseph M. Rosplock, Caledonia, both of Wis.

[73] Assignee: S. C. Johnson & Son, Inc., Racine, Wis.

[21] Appl. No.: 645,975

[22] Filed: May 14, 1996

[51] Int. Cl.$^6$ ........................................................ A61L 9/04
[52] U.S. Cl. ................................................................ 239/58
[58] Field of Search ................................. 239/54, 57–59

[56] References Cited

U.S. PATENT DOCUMENTS

| | | |
|---|---|---|
| Re. 32,513 | 10/1987 | Seaber et al. . |
| Re. 35,513 | 5/1997 | Saeber et al. ........................ 239/54 X |
| 2,481,296 | 9/1949 | Dupuy . |
| 2,594,714 | 4/1952 | Andre . |
| 2,720,419 | 10/1955 | Eby ....................................... 239/55 X |
| 3,343,664 | 9/1967 | Poitras .................................. 239/57 X |
| 3,790,081 | 2/1974 | Thornton et al. . |
| 3,946,945 | 3/1976 | Odioso et al. . |
| 4,130,245 | 12/1978 | Bryson . |
| 4,145,001 | 3/1979 | Weyenberg . |
| 4,157,787 | 6/1979 | Schwartz . |
| 4,158,440 | 6/1979 | Sullivan et al. . |
| 4,220,281 | 9/1980 | Martenz, III et al. . |
| 4,285,468 | 8/1981 | Hyman ....................................... 239/55 |
| 4,306,679 | 12/1981 | Dusek et al. . |
| 4,382,548 | 5/1983 | van der Heijden . |
| 4,502,630 | 3/1985 | Haworth et al. . |
| 4,558,820 | 12/1985 | Harris, Jr. . |
| 4,572,375 | 2/1986 | Baer ....................................... 239/56 X |
| 4,583,686 | 4/1986 | Martens et al. . |
| 4,595,925 | 6/1986 | Hansen . |
| 4,605,165 | 8/1986 | Van Loveren et al. . |
| 4,615,486 | 10/1986 | Konicek . |
| 4,630,775 | 12/1986 | Mandon et al. . |
| 4,660,763 | 4/1987 | Gutkowski et al. . |
| 4,739,928 | 4/1988 | O'Neil . |
| 4,849,606 | 7/1989 | Martens, III et al . |
| 4,923,119 | 5/1990 | Yamamoto et al. ........................ 239/55 |
| 4,948,047 | 8/1990 | Zembrodt . |
| 4,960,240 | 10/1990 | McElfresh . |
| 4,983,578 | 1/1991 | Cashman et al. . |
| 4,998,671 | 3/1991 | Leifheit . |
| 5,439,100 | 8/1995 | Gordon et al. . |

FOREIGN PATENT DOCUMENTS 631248  12/1927  France ........................................ 239/55

Primary Examiner—Kevin Weldon

[57] ABSTRACT

This invention provides an air freshener dispenser device in the form of a semi-rigid thermoplastic strip, which has the central area of both flat surfaces covered with a coextensive laminate of an inner vapor-permeable membrane and an outer peelable vapor-impermeable membrane. The respective membrane laminates enclose the central area of the strip which has at least one aperture accessing between the two laminate films. Preferably there are multiple apertures which serves as a reservoir for a volatile air freshener ingredient. Partial or complete removal of one or both peelablevapor-impermeable membranes allows delivery of the air freshener ingredient as vapor into the environment at a controlled rate over an extended time period.

9 Claims, 2 Drawing Sheets

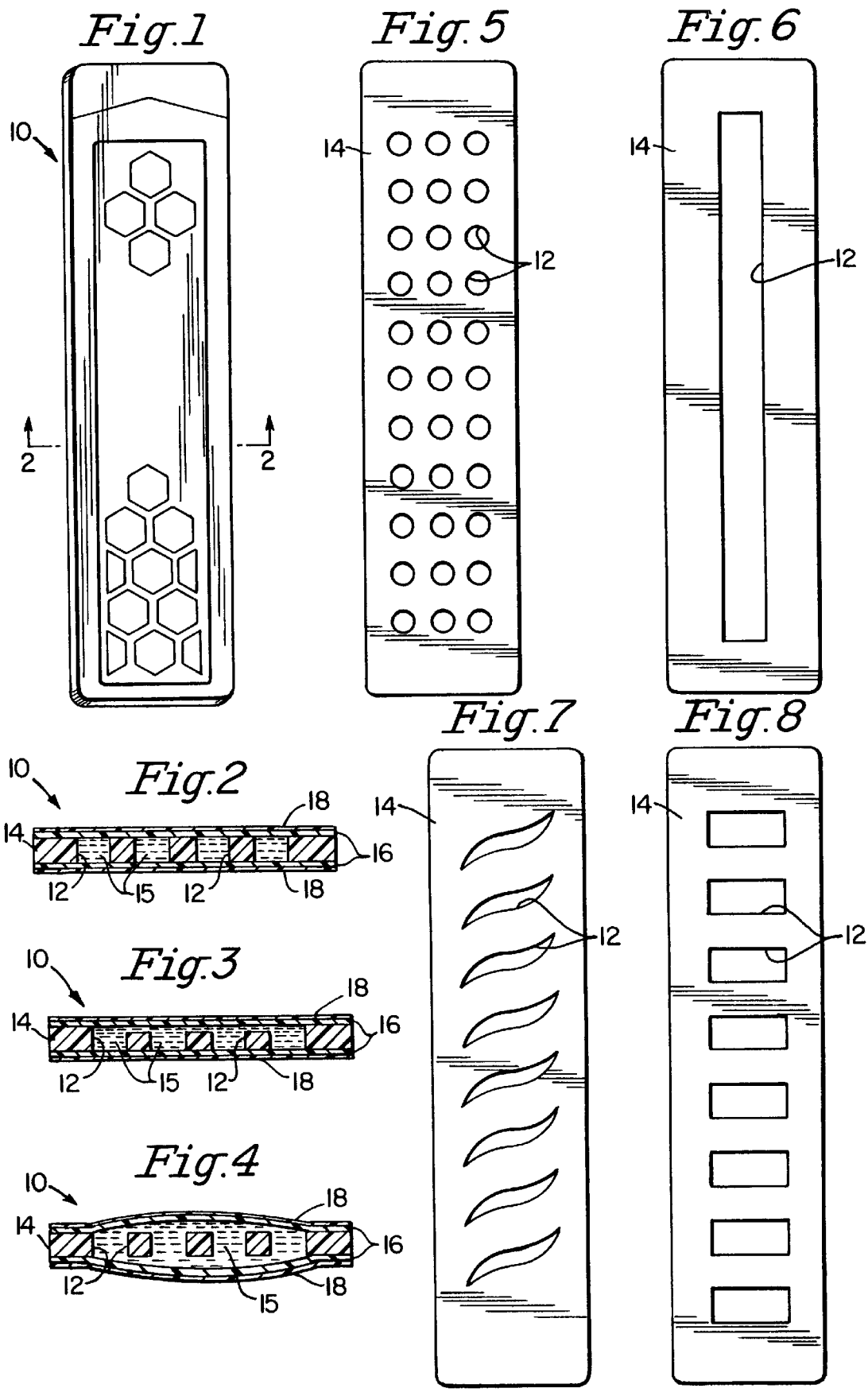

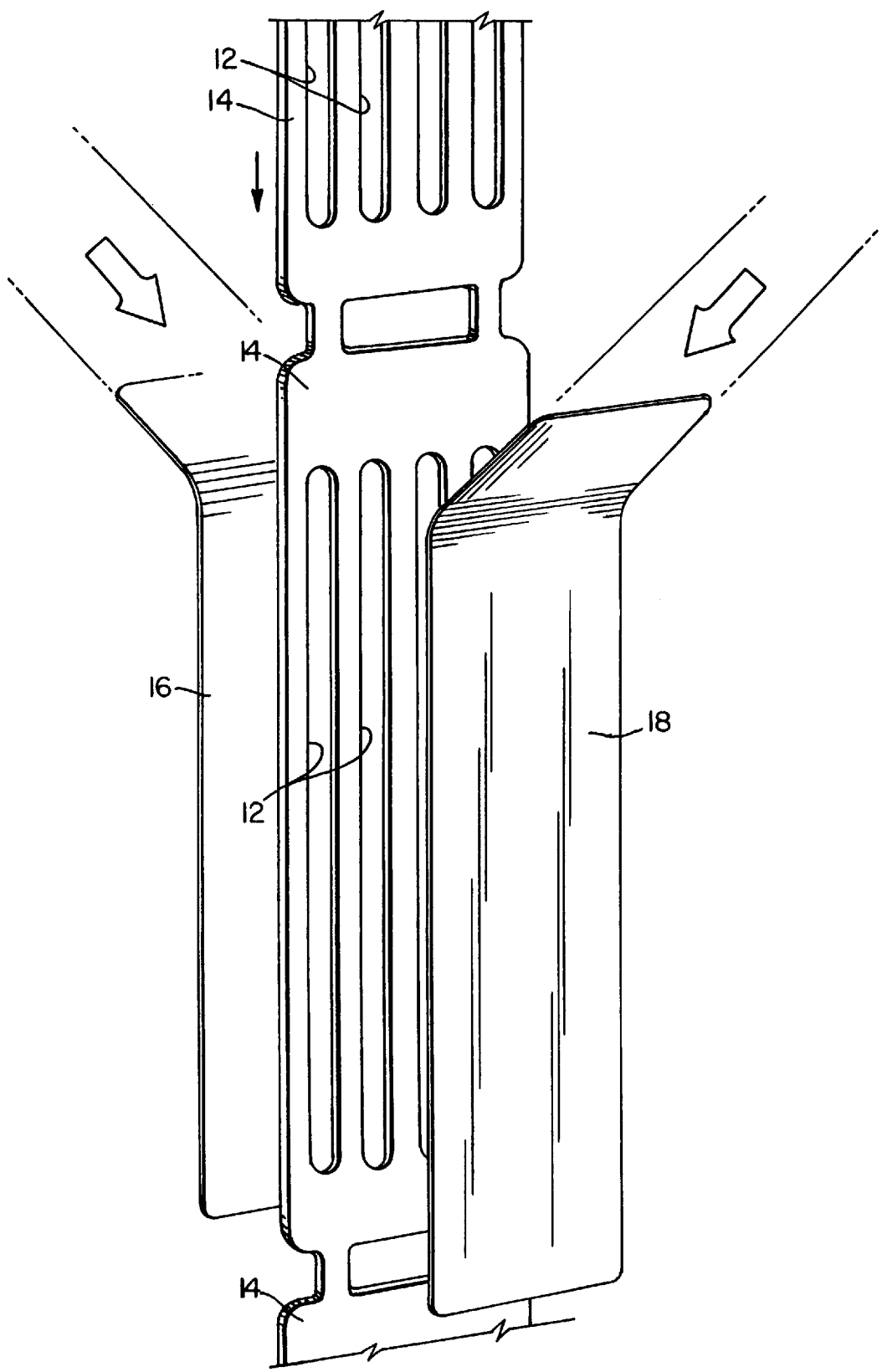

AIR FRESHENER DISPENSER DEVICE

BACKGROUND OF THE INVENTION

This invention generally relates to dispensers of vaporizable media. More specifically, this invention relates to a device for dispensing a fragrance or deodorant in the form of a vapor for air freshening in an enclosed environment.

The need for effectively combating airborne malodors in homes and enclosed public buildings, by odor masking or destruction, is well established. Various kinds of vapor-dispensing devices have been employed for this purpose. The most common of such devices is the aerosol container which propels minute droplets of an air freshener composition into the air. Another common type of dispensing device is a dish containing or supporting a body of gelatinous matter which when it dries and shrinks releases a vaporized air-treating composition into the atmosphere. Other products such as deodorant blocks and liquid wicks are also used for dispensing air-treating vapors into the atmosphere by evaporation. Another group of vapor-dispensing devices utilizes a carrier material such as paperboard impregnated or coated with a vaporizable composition.

A number of recent developments include a liquid air-treating composition in an enclosure, all or part of which is formed of a polymeric film through which the air-treating composition can migrate to be released as a vapor at an outer surface. Use of this type of permeable polymeric membrane controls the dispensing of air-treating vapors and tends to eliminate great variations in the rate of dispensing over the life of the product. Such products are considered advantageous when compared with the many air-treating products for which the rate of vapor release drops substantially over the life of the product.

Products of the type having a sheet of permeable polymeric material to control the emission of air-treating vapors may be in a variety of forms. In some, the polymeric sheet covers a cylindrical container, while in others the liquid air-treating material is trapped between the permeable sheet and an impermeable plastic sheet. In still others, the permeable polymeric material forms a flexible pouch having a content of the air-treating liquid. The liquid, prior to activation, is isolated within a breakable container such as a glass vial or an impermeable plastic inner pouch, or the like.

Publications of background interest in connection with air freshener devices include U.S. Pat. Nos. 2,481,296; 2,594,714; 3,790,081; 3,946,945; 4,130,245; 4,145,001; 4,220,281; 4,306,679; 4,382,548; 4,502,630; 4,558,820; 4,583,686; 4,595,925; 4,615,486; 4,660,763; 4,630,775; 4,739,928; 4,849,606; 4,948,047; 4,960,240; 4,983,578; 4,998,671; and the like; incorporated by reference.

Some air freshener dispensers are expensive to manufacture. Other air freshener dispensers are inexpensive to produce, but tend to have inferior construction and functionality.

There remains a need for a well-constructed air freshener dispenser device which can be mass-produced economically and which can deliver a vapor medium at a controlled uniform rate over an extended period of time.

Accordingly, it is an object of this invention to provide an improved air freshener dispenser device for delivering an odorant and/or deodorant vapor in an enclosed environment.

It is another object of this invention to provide an air freshener dispenser device with a primary structure which is a semi-rigid plastic strip that can be produced economically by a thermoforming means in a continuous process.

It is a further object of this invention to provide a rigidly supported reservoir enclosure which has a volatile air freshener content, and which is sandwiched between two translucent or transparent permeable membranes.

Other objects and advantages of the present invention shall become apparent from the accompanying description and drawings.

SUMMARY OF THE INVENTION

One or more objects of the present invention are accomplished by the provision of an air freshener dispenser device comprising:

(a) a thin semi-rigid strip with a planar periphery that frames a central section which has at least one aperture accessing the coextensive flat surfaces;

(b) a thin membrane on each flat surface of the strip, which covers and seals the perforated central section and forms a reservoir enclosure, and which is permeable to a volatile medium in the reservoir enclosure;

(c) A volatile air freshener ingredient which is contained within the reservoir enclosure; and (d) a thin peelable impermeable membrane which is bonded coextensively with each respective permeable membrane to prevent volatilization of the air freshener ingredient through the permeable membrane from the reservoir enclosure.

DESCRIPTION OF THE DRAWINGS

FIG. 1 is a perspective view of an invention air freshener dispenser device with an imprinted design.

FIG. 2 is a sectional view taken along lines 2—2 of FIG. 1.

FIGS. 3–4, respectively, illustrate alternative reservoir configurations for the volume of air freshener ingredient taken along lines 2—2 of FIG. 1.

FIGS. 5–8, respectively, illustrate aperture configurations in a semi-rigid thermoplastic structure of an invention air freshener.

FIG. 9 is an exploded perspective view of a stage in the assembly of an invention air freshener dispenser device in a continuous manufacturing process.

DESCRIPTION OF THE PREFERRED EMBODIMENTS

FIG. 1 illustrates a present invention air freshener dispenser device which has a design imprinted on its upper surface.

A FIG. 1 type of air freshener dispenser device has a semi-rigid structure, and its typical dimensions are about four inches in length, about one half to one inch in width, and about one sixteenth to one fourth inch in thickness.

A FIG. 1 type of air freshener dispenser device can be utilized by peeling one of the outer impermeable membranes partially or completely, or peeling the outer impermeable membrane from each side of the dispensing device.

FIG. 2 is a cross-sectional end view of a FIG. 1 type of air freshener dispenser device which has an elongated grating of parallel apertures 12 in semi-rigid strip 14.

FIG. 3 is a cross-sectional end view similar to FIG. 2, in which the parallel grating rib sections of strip 14 are slightly recessed to provide a greater reservoir capacity for air freshener ingredient 15. FIG. 4 is a cross-sectional view similar to FIG. 2, in which membranes 16 and 18 are in a convex configuration to provide an increased capacity for air freshener ingredient 15 in addition to the aperture 12 volume.

Other aperture configurations are represented in FIGS. 5–8. Apertures 12 have a content of volatile air freshener ingredient 15. Thin film vapor-permeable membrane 16 is coextensive with each flat surface of strip 14, and forms a sealed bond along the periphery margin of strip 14. Apertures 12 are enclosed within the sealed cross-section of permeable membrane 16 on each side of strip 14.

Thin film vapor-impermeable membrane 18 is bonded to vapor-permeable membrane 16 in the form of a laminate. Vapor-impermeable membrane 18 is peelable, so that its partial or complete removal allows air freshener ingredient 15 to migrate through vapor-permeable membrane 16 and volatilize into the atmosphere.

Semi-rigid strip 14 can be constructed by either injection or thermoform molding of a thermoplastic polymer such as polyethylene, polypropylene, polyvinyl chloride, and the like.

Vapor-permeable membrane 16 can be in the form of a flexible thin film of a thermoplastic polymer such as polyethylene, isotactic polypropylene, cellulose acetate, and the like. Membrane 16 permits migration of the enclosed volatile air freshener ingredient 15, either as a liquid or a vapor, depending on the type of membrane 16 being employed. Membrane 16 can be a microporous type (submicron pores), such as isotactic hydrophobic polypropylene film sold under the CELGARD tradename (Celanese). Microporous thermoplastic polymer films are described in U.S. Pat. No. 3,055,297; incorporated by reference.

Vapor-impermeable membrane 18 can be in the form of a flexible thin film such as aluminum foil or nylon film, which is peelable from its adhering bond to vapor-permeable membrane 16.

In a preferred embodiment a laminate of membrane 16 and membrane 18 is preformed, and then applied to semi-rigid strip 14 and heat-sealed along the periphery margin of strip 14 to enclose the reservoir content of air freshener ingredient 15. Production of a laminate of permeable and impermeable membranes is illustrated in U.S. Pat. No. 4,145,001; incorporated by reference.

Air freshener ingredient 15 can be any air treating material which can migrate through membrane 16 and disperse into the atmosphere in vapor form. Typically air freshener ingredient 15 is a fragrance or a deodorant in liquid or gel form.

Preferably, air freshener ingredient 15 is a liquid fragrance comprising one or more volatile organic compounds which are available from perfumery suppliers such as Firmenich Inc., Takasago Inc., Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

A fragrance ingredient also can be in the form of a crystalline solid, which have the ability to sublime into the vapor phase at ambient temperatures. A crystalline fragrance starting material can be selected from organic compounds which include vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evernyl, and the like. This type of fragrance can contribute a long term air-treating capability to an air freshener dispenser device.

In a further embodiment this invention provides a continuous process for the manufacture of a present invention air freshener dispenser device as illustrated in FIG. 9, which process comprises (1) providing a moving band of semi-rigid thermoplastic polymer, wherein the band has repeating unitary sections having correspondence with strip 14 in FIG. 9; (2) providing a moving band of a flexible membrane laminate in contacting and sealing proximity with the underside of the semi-rigid thermoplastic band, wherein the membrane laminate has repeating unitary sections having proximal and dimensional correspondence with the unitary sections of the semi-rigid thermoplastic band, and wherein the membrane laminate is composed of an inner vapor-permeable thin film, and a coextensive outer vapor-impermeable thin film; (3) providing means for filling the aperture spacing in the moving semi-rigid thermoplastic band with a volatile air freshener ingredient; (4) providing a second band of the flexible membrane laminate in contacting and sealing proximity with upperside of the thermoplastic band; and (5) cutting and trimming the unitary sections to provide a present invention air freshener dispenser device in a high volume rate of production.

FIG. 9 demonstrates an intermediate stage mobility of a band of semi-rigid strip 14 units, and two bands of laminate units of vapor-permeable membrane 16 and vapor-impermeable membrane 18, in a continuous process for manufacture of an invention air freshener dispenser device as illustrated in FIG. 1. A means for filling the apertures with a volatile air freshener ingredient is not shown in FIG. 9.

A present invention air freshener device can be produced in high volume from relatively inexpensive plastic materials. After usage, the device qualifies for disposal as a non-hazardous solid waste.

The present invention also contemplates an integrated combination of a FIG. 1 type air freshener device and a dispensing holder structure. The FIG. 1 device then functions as a replaceable refill cartridge.

What is claimed is:

1. An air freshener dispenser device comprising:
   (a) a thin semi-rigid strip with a planar periphery that frames a central section which has at least one aperture accessing coextensive flat surfact of the strip;

(b) a thin membrane on each flat surface of the strip, which is fixed about the entire planar periphery and which covers and seals the perforated central section and forms a reservoir enclosure, and which is permeable to a volatile medium in the reservoir enclosure;

(c) a volatile air freshener ingredient which is contained within the reservoir enclosure; and (d) a thin peelable impermeable membrane which is bonded coextensively with each respective permeable membrane to prevent volatilization of the air freshener ingredient through the permeable membrane from the reservoir enclosure.

2. A dispenser device in accordance with claim 1 wherein the semi-rigid strip is a molded thermoplastic structure.

3. A dispenser device in accordance with claim 1 wherein the semi-rigid strip is a molded polyethylene or polypropylene structure.

4. A dispenser device in accordance with claim 1 wherein the permeable membrane is a polyvinyl thin film.

5. A dispenser device in accordance with claim 1 wherein the impermeable membrane is an aluminum foil or nylon film.

6. A dispenser device in accordance with claim 1 wherein the volatile air freshener is a fragrance in a liquid, gel or crystalline form.

7. A dispenser device in accordance with claim 1 wherein the respective permeable membranes have transparency, and the content of a volatile air freshener ingredient in the reservoir enclosure is visible.

8. A dispenser device in accordance with claim 1 wherein the outer impermeable membrane is imprinted with a logo design.

9. A dispenser device in accordance with claim 1 which is incorporated in a dispensing holder structure, and functions as a replaceable refill cartridge.

* * * * *

UNITED STATES PATENT AND TRADEMARK OFFICE
CERTIFICATE OF CORRECTION

PATENT NO. : 5,845,847
DATED : Dec. 8, 1998
INVENTOR(S) : John Martin et al.

It is certified that error appears in the above-identified patent and that said Letters Patent is hereby corrected as shown below:

<u>In the Claims</u>:

Claim 1, line 4, please delete "surfact" and insert --surfaces--.

Signed and Sealed this

Twelfth Day of December, 2000

Attest:

Q. TODD DICKINSON

*Attesting Officer*      *Director of Patents and Trademarks*